(12) United States Patent
Whitmer

(10) Patent No.: US 9,910,510 B1
(45) Date of Patent: Mar. 6, 2018

(54) MEDICAL CODING KEYBOARD

(71) Applicant: Elizabeth Whitmer, Ft. Myers Beach, FL (US)

(72) Inventor: Elizabeth Whitmer, Ft. Myers Beach, FL (US)

(*) Notice: Subject to any disclaimer, the term of this patent is extended or adjusted under 35 U.S.C. 154(b) by 0 days.

(21) Appl. No.: 15/663,776

(22) Filed: Jul. 30, 2017

(51) Int. Cl.
*G06F 3/02* (2006.01)
*G09G 5/00* (2006.01)
*G06F 3/023* (2006.01)
*G06Q 50/22* (2018.01)

(52) U.S. Cl.
CPC .......... *G06F 3/0219* (2013.01); *G06F 3/0233* (2013.01); *G06Q 50/22* (2013.01)

(58) Field of Classification Search
CPC .................................................... G06F 3/0219
USPC ........................................................ 345/168
See application file for complete search history.

(56) References Cited

U.S. PATENT DOCUMENTS

| 2,040,248 | A | | 5/1932 | Dvorak | |
| 5,682,151 | A | * | 10/1997 | Oliveros | G06F 3/0219 |
| | | | | | 341/23 |
| 6,142,687 | A | * | 11/2000 | Lisak | G06F 3/0213 |
| | | | | | 400/472 |
| 7,023,364 | B2 | | 4/2006 | Rose | |
| 8,405,601 | B1 | * | 3/2013 | Beale | G06F 3/0219 |
| | | | | | 345/156 |
| 2003/0021032 | A1 | * | 1/2003 | Bamji | G06F 3/038 |
| | | | | | 359/568 |
| 2006/0257191 | A1 | * | 11/2006 | Artus | G06F 3/0216 |
| | | | | | 400/486 |
| 2010/0328235 | A1 | | 12/2010 | Taute | |
| 2011/0227829 | A1 | * | 9/2011 | Barr | G06F 3/0202 |
| | | | | | 345/168 |
| 2015/0142470 | A1 | | 5/2015 | Glenn | |
| 2017/0032087 | A1 | | 2/2017 | Tanase | |

OTHER PUBLICATIONS

Microsoft's Sculpt Ergonomic Keyboard, webpage https://marco.org/2013/08/30/sculpt-ergonomic-keyboard-review, downloaded Apr. 25, 2017.
Custom Keyboard for Apple products, webpage—https://developer.apple.com/library/content/documentation/General/Conceptual/ExtensibilityPG/CustomKeyboard.html, downloaded Apr. 25, 2017.

(Continued)

*Primary Examiner* — Long D Pham
(74) *Attorney, Agent, or Firm* — Guy Cumberbatch

(57) ABSTRACT

A keyboard specifically designed to reduce errors in medical coding and aid in the coding process by making it easier to locate only the keys needed to accomplish coding. The keyboard moving the I and O to a different location than the remaining 24 alphabetic characters, and arranges those 24 characters in alphabetic sequence. The keyboard may have a first key group having the alphabetic keys inclusive of all the letters of the alphabet except for the letters I and O, a second key group including the numeric keypad and the letters I and O, and a third key group having only function keys. The keyboard increases coding volume by requiring less time than searching a standard QWERTY keyboard for the necessary keys and consequently helps to cut down on coding errors.

20 Claims, 3 Drawing Sheets

(56) References Cited

OTHER PUBLICATIONS

Custom Keyboard for Android products, webpage—htttps://code.tutsplus.com/tutorials/create-a-custom-keyboard-on-android--cms-22615, downloaded Apr. 25, 2017.

Coding-Keyboard-App, Google Play Store entry—htttps://play.google.com/store/apps/details?id=com.gazlaws.codeboard&hl=en, downloaded Apr. 24, 2017.

Toms_Guide-best-android-keyboards, webpage—https://www.tomsguide.com/us/pictures-story/403-best-android-keyboard-apps.html#s17, available Jul. 29, 2017.

\* cited by examiner

MEDICAL CODING KEYBOARD

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

This disclosure relates to a computer keyboard and, more particularly, to a keyboard designed for medical coding and reducing mistakes when coding.

Description of the Related Art

Medical coding is the transformation of healthcare diagnosis, procedures, medical services, and equipment into universal medical alphanumeric codes. The diagnoses and procedure codes are taken from medical record documentation, such as transcription of physician's notes, laboratory and radiologic results, etc. Medical billing and coding workers are the health care professionals in charge of processing patient data such as treatment records and related insurance information. Medical insurance billers and coders are tasked with coding a patient's diagnosis along with a request for payments from the patient's insurance company. Medical coding professionals transfer these codes from the sources to medical billing systems and patient records. Medicare, Medicaid and $3^{rd}$ Party insurance companies receive billing invoices and patient health information along with the coded data.

On Oct. 1, 2015, the U.S. Department of Health and Human Services (HHS) mandated that all entities covered by the Health Insurance Portability and Accountability Act (HIPAA) must transition to a new set of codes for electronic health care transactions. This transformation replaced the protocol of ICD-9-CM, used since 1979, with ICD-10-CM/PCS, and increased the volume of codes tremendously. As of February 2010, ICD-9-CM had a total of 14,315 distinct diagnostic codes, while ICD-10-CM had 69,101 codes. This huge expansion allows for a lot more specificity and detail, reflecting the advances in clinical medicine over the last several decades. However, medical coders had to learn coding all over again. Adding the new coding standards and rules has slowed down production and created many coding errors, reflecting in "denials" from Medicare, Medicaid and $3^{rd}$ party insurance companies.

Due to the recent implementation of the ICD-10-CM coding protocol, there is a need for tools and practices to help medical coders reduce errors.

SUMMARY OF THE INVENTION

According to exemplary embodiments, a keyboard specifically designed to reduce errors in medical coding is disclosed. The exemplary keyboard aids in the coding process by making it easier to locate "ONLY" the keys needed to accomplish coding. The keyboard also increases coding volume by requiring less time searching a standard QWERTY keyboard for the necessary keys. It also helps to cut down on coding errors by moving the I and O to a different location.

An exemplary keyboard useful for medical coding as disclosed herein comprises a housing enclosing keyboard circuitry and framing a plurality of keys connected to the circuitry and segregated into key groups. There is a first key group having just alphabetic keys inclusive of all the letters of the alphabet except for the letters I and O. Additionally, a second key group spaced from the first key group on the housing across a key gap includes a numeric keypad with the digits 0-9 and alphabetic keys with the letters I and O. There may also be a third key group spaced from both the first and second key groups and having only function keys. The keyboard housing preferably has a width W of between about 25-30 cm, and a height H of between about 15-20 cm.

A second exemplary keyboard useful for medical coding includes a keyboard defining a keyboard face having a width W of between about 25-30 cm, and a height H of between about 15-20 cm. The keyboard face has separate character keys segregated into a plurality of key groups spatially separated from each other across key gaps, wherein a first one of the key groups includes alphabetic keys inclusive of all the letters of the alphabet except for the letters I and O, and a second key group includes the alphabetic keys for the letters I and O.

And finally a third exemplary keyboard useful for medical coding disclosed herein comprises a first key group having alphabetic character keys arrayed in alphabetical order in a plurality of rows and columns inclusive of all the letters of the alphabet except for the letters I and O. The keyboard further has keys for the letters I and O spaced from the first key group across a key gap, and there are a maximum of forty-seven (47) total keys and all of the alphabetical keys are shown and configured to trigger key signals in uppercase with no shift key to permit them to convert to lowercase. Preferably, the letters I and O are placed in a second key group spaced from the first key group across a key gap which also includes a numeric keypad with the digits 0-9.

In each of the exemplary keyboards there are preferably a total of no more than forty-seven total keys, and in one embodiment a total of forty-five keys. The second key group one the keyboard desirably includes function keys. All alphabetic keys display uppercase letters and the circuitry is configured to send uppercase letter signals, and there is no shift key to switch to lowercase letters on the keyboard. Preferably, the alphabetic keys in the first key group are arranged in rows and columns in alphabetical order from the top left continuing along each row to the bottom right. If there is a third key group spaced from both the first and second key groups it may have only function keys. The keyboards may be standalone items with a plastic keyboard housing defining the keyboard face, or may be virtual keyboards superimposed on a display screen.

Other features and characteristics of the present invention, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

Furthermore, unless otherwise stated, any specific dimensions mentioned in this description are merely representative of an exemplary implementation of a device embodying aspects of the invention and are not intended to be limiting.

Figure 1:
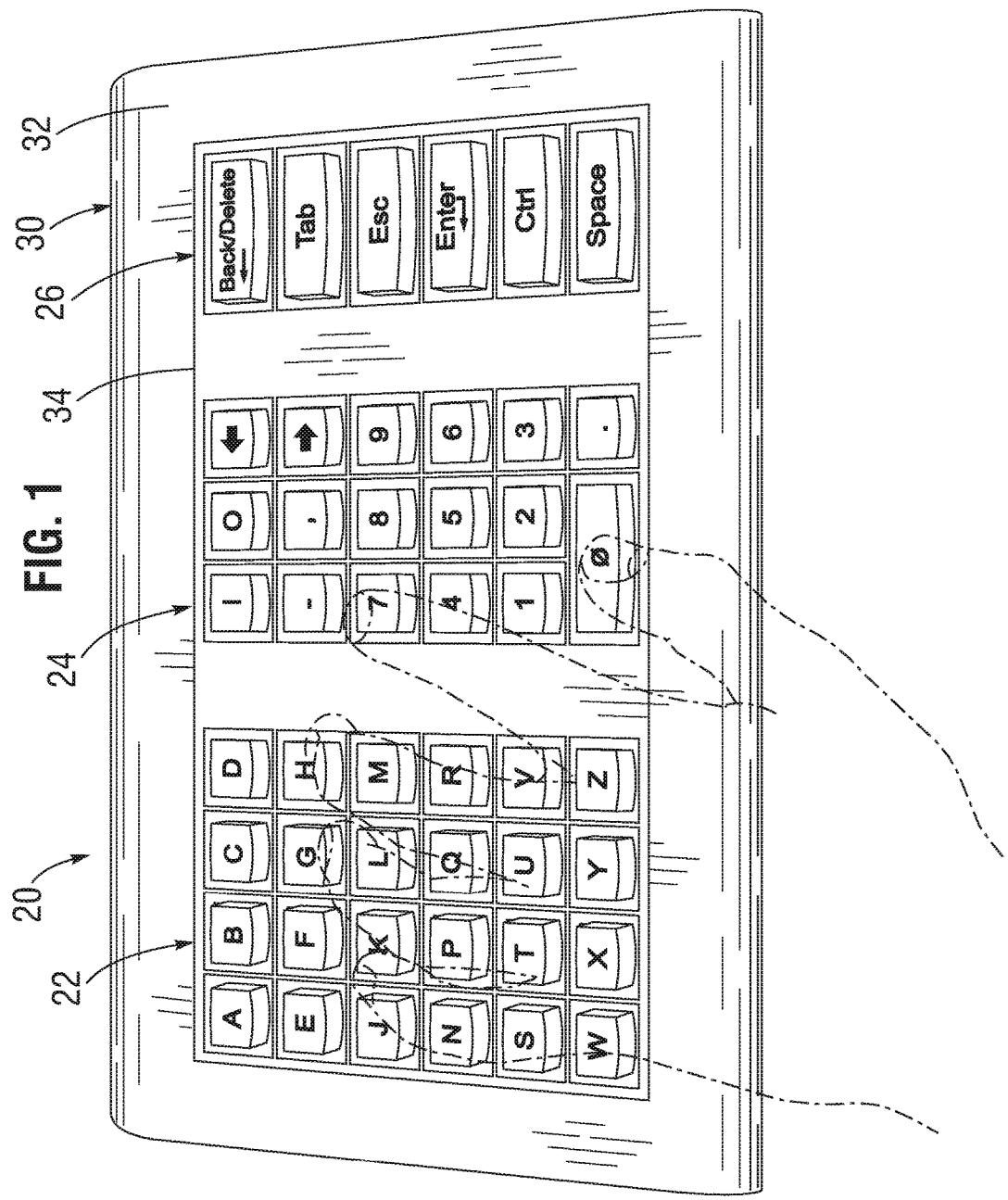
FIG. 1 is a perspective view of an exemplary medical coding keyboard of the present application showing in phantom a hand of a user in the process of typing.

FIG. 1 is a perspective view of an exemplary medical coding keyboard 20 of the present application showing in phantom a hand of a user in the process of typing on it. The keyboard 20 is much smaller than the standard "QWERTY" keyboard, the keys are segregated into different groups, and the alphabetic keys are rearranged.

Standard QWERTY keyboards have been around for more than a century. The so-called QWERTY typewriter keyboard was designed to keep letters commonly used together away from each other to prevent jamming. Early iterations of the keyboard were devised in the late 1800s for the then typewriter. The term "QWERTY" came to describe this keyboard format because these six letters are present in sequence starting at the left side of the top row of the alphabetic characters. Although alternate keyboards tried to break onto the market, most people decided to stay with the QWERTY board, and none of the other type-writing machines proved successful. Eventually, computer keyboards adopted the same general layout of the alphabetic characters with a row of numbers along the top and other functional keys added around the outer edges. There have been localized variations to QWERTY, including QWERTZ (common in Central Europe), AZERTY (common in France), and QZERTY (mostly used in Italy). Three other notable but less-recognized layouts are Workman, Qwpr, and Minimak, though these are more proofs-of-concept than actual layouts intended for everyday use. These variations are ultimately minor; they all mostly just re-arrange the alphabetic characters while keeping them all grouped together in two or three rows.

Figure 2:
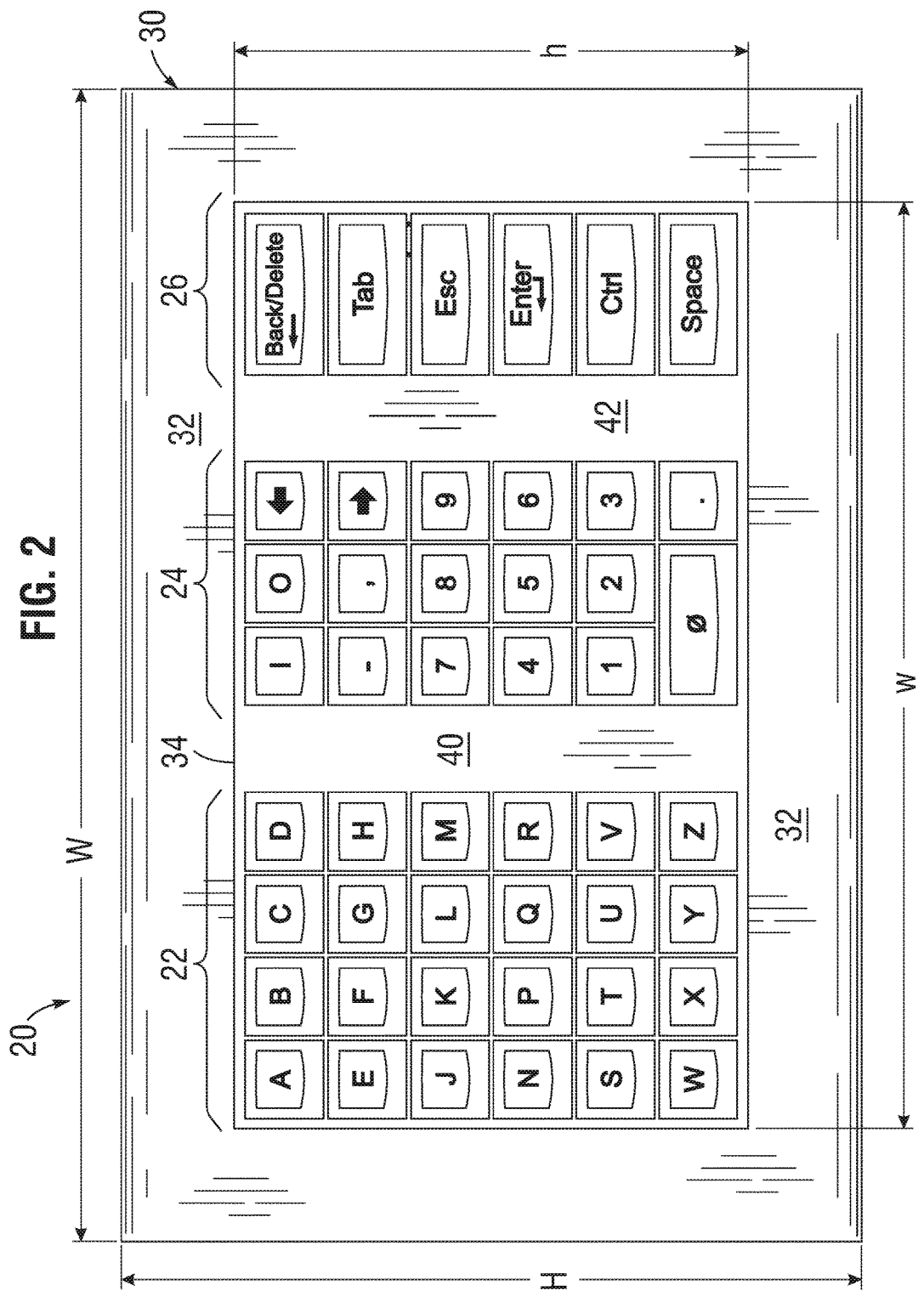
FIG. 2 is a top plan view of the exemplary keyboard.

As seen in both FIGS. 1 and 2, the exemplary keyboard 20 radically rearranges the various keys on its upper face into three groups: a first key group 22 of exclusively alphabetic character keys, a second key group 24 of mixed alphanumeric and function keys, and a third key group 26 of exclusively function keys. The keyboard 20 has a generally rectangular housing 30 defining a frame or border region 32 surrounding a central rectangular keyboard face or key region 34. The border region 32, as with most keyboards, features no keys and provides a surface on which to rest one's hands while typing, or between typing spells. The border region 32 is preferably about 2.6 cm (1 inch) in width, although smaller or larger borders may be preferred.

The overall size of the rectangular housing 30 is modified from conventional rectangular computer keyboards in that the width W is reduced, primarily by elimination of a second set of numerical keys, and a number of typical functional keys. For example, most rectangular computer keyboards include a row of numerical keys above the alphabetic keys, and also a separate number pad on the right side, which is redundant. Furthermore, most modern computer keyboards include a row of function keys along the top edge, which is not needed for the present medical coding keyboard 20. Indeed, standard long keyboards typically have 104 keys, while the exemplary keyboard 20 has only 45 necessary coding keys. Moreover, the key letters are always in capitol font, and there is no way to shift back to lowercase.

Preferably, the width W of the keyboard 20 is between about 25-30 cm, and more preferably about 26.5 cm, while a conventional computer keyboard may be more than 40 cm wide. The height H of the keyboard 20 is preferably between about 15-20 cm, and more preferably about 17 cm. In the illustrated embodiment, the rectangular key region 34 has a width w of between about 20-24 cm, and more preferably about 21.3 cm, and a height h of between about 10-13 cm, and preferably about 11.8 cm. The preferred dimensions leave a border region 32 around the key region 34 of between about 2-4 cm, and more preferably about 2.6 cm.

It should be noted that the keyboards disclosed herein may be standalone, tangible items typically with a plastic keyboard housing surrounding the keyboard face that are connected directly or via wireless technology to a processor. Alternatively, the keyboard face may be generated by software/firmware as a "virtual" keyboard for display on a variety of display screens. Currently there are apps and other such options for designing such virtual keyboards, mainly for customizing smart phone keyboard options (see, e.g., https://www.tomsguide.com/us/pictures-story/403-best-android-keyboard-apps.html). However, most of these are concerned with making texting easier, adding shortcuts and function keys, more emojis and the like, all retain the QWERTY layout, and no such virtual apps are available for medical coding. The present application contemplates software that displays and operates the medical coding keyboards and key layouts disclosed herein on a variety of display surfaces. The particular display surface such as a smartphone screen, tablet screen, or the like provides the "keyboard face" on which the various key groups are arranged.

The first key group 22 is desirably positioned on the left side of the key region 34, the second key group 24 in the middle, and the third key group 26 is on the right side. The first key group 22 may alternatively be positioned on the right side of the key region 34 to accommodate alternate-handed users or preference. A first key gap 40 is provided between the right side of the first key group 22 and the side of the second key group 24, and a second key gap 42 is provided between the right side of the second key group 24 and the left side of the third key group 26. These key gaps 40, 42 are preferably extensions of the housing 30 or areas of a solid panel within the key region that is absent of keys. The key gaps 40, 42 effectively segregate the three groups 22, 24, 26, and facilitate accurate typing on the coding keyboard 20 by reducing accidental keystrokes between the groups. The gaps 40, 42 are preferably between about 2-3 cm wide, and extend the full height h of the key region 34.

In the illustrated embodiment, there are six rows of keys in each group from top to bottom. In the first key group 22, the alphabetic keys are arranged in alphabetical order with "A" at the top left, and "Z" at the bottom right, in four columns distributed in the six rows—i.e., from the top left continuing to the right along each row down to the bottom right. This totals 24 keys, comprising all 26 alphabetical letters except the "I" and the "O" keys. The 24 alphabetic keys are all shown in uppercase, which is common in conventional computer keyboards, however there is no shift option and the circuitry associated with the keyboard 20 only permits uppercase. That is, there are no lowercase alphabetic keystrokes available on the keyboard 20, which again is optimized for medical coding which does not use lowercase letters.

The second key group 24 in the middle of the key region 34 includes three columns of keys for the first five rows from the top, but only two keys in the bottom row, for a total of 17 keys. The "I" and the "O" keys appear in the top row along with the left arrow key. The second row down includes a hyphen or dash key, a comma key, and the right arrow key. The third fourth and fifth rows down provide a conventionally arranged numeric keypad for the digits 1-9, and the bottom or sixth row includes an oversized zero-digit key along with a period key. The lower four rows are thus arranged in the same manner that a conventional numeric keypad on standard computer keyboards is arranged. The hyphen or dash key, the comma key, and the period key provide the only three punctuation keys on the entire keyboard 20, which is all that is considered necessary for medical coding.

Finally, the third key group 26 on the right side of the key region 34 has six oversized function keys. From top to bottom, the keys include the back/delete key, the tab key, the escape key, the enter key, the control key, and the space key. These, along with the left and right arrow keys in the second key group 24, are the only function keys that are deemed necessary for medical coding. There may be one or more additional function keys if desired, though the six shown are considered essential.

Consequently, the twenty-four alphabetic keys in the first key group 22, plus the seventeen in the second key group 24 and the minimum of six keys in the third key group 26 totals forty-seven (47) keys.

Aside from grouping the alphabetic keys in the first key group 22 in alphabetical order, rather than in the standard QWERTY format, it is important to understand the reason for segregating the "I" and the "O" keys into the second key group 24.

The new protocol ICD-10-PCS utilizes 7-digit codes, where the characters can be either alpha or numeric. However, the letters "I" and "O" are not used to avoid confusion with the numbers 1 and 0. The $2^{nd}$ and $3^{rd}$ digits are numeric while the $4^{th}$, $5^{th}$, $6^{th}$ and $7^{th}$ digits can be alpha or numeric. A one ("1") or zero ("0") is placed after the first 3 characters. Two examples are 0FB03ZX—Excision of Liver, Percutaneous Approach, Diagnostic, and 0DQ10ZZ—Repair upper esophagus, open approach.

Accordingly, although the "I" and "O" keys remain on the keyboard 20, they are segregated into the second key group 24 because they are not used in the ICD-10-PCS coding standard. Instead, they appear above the numerical keys in the second key group 24, and stand out clearly therefrom to avoid mistakenly using them for the 1 or the 0. Furthermore, the remaining 24 alphabetic keys are arranged in alphabetical sequence, which is much more intuitive for the medical coder who otherwise would have to rely on muscle memory or search for the letters on the standard QWERTY keyboard.

Figure 3:
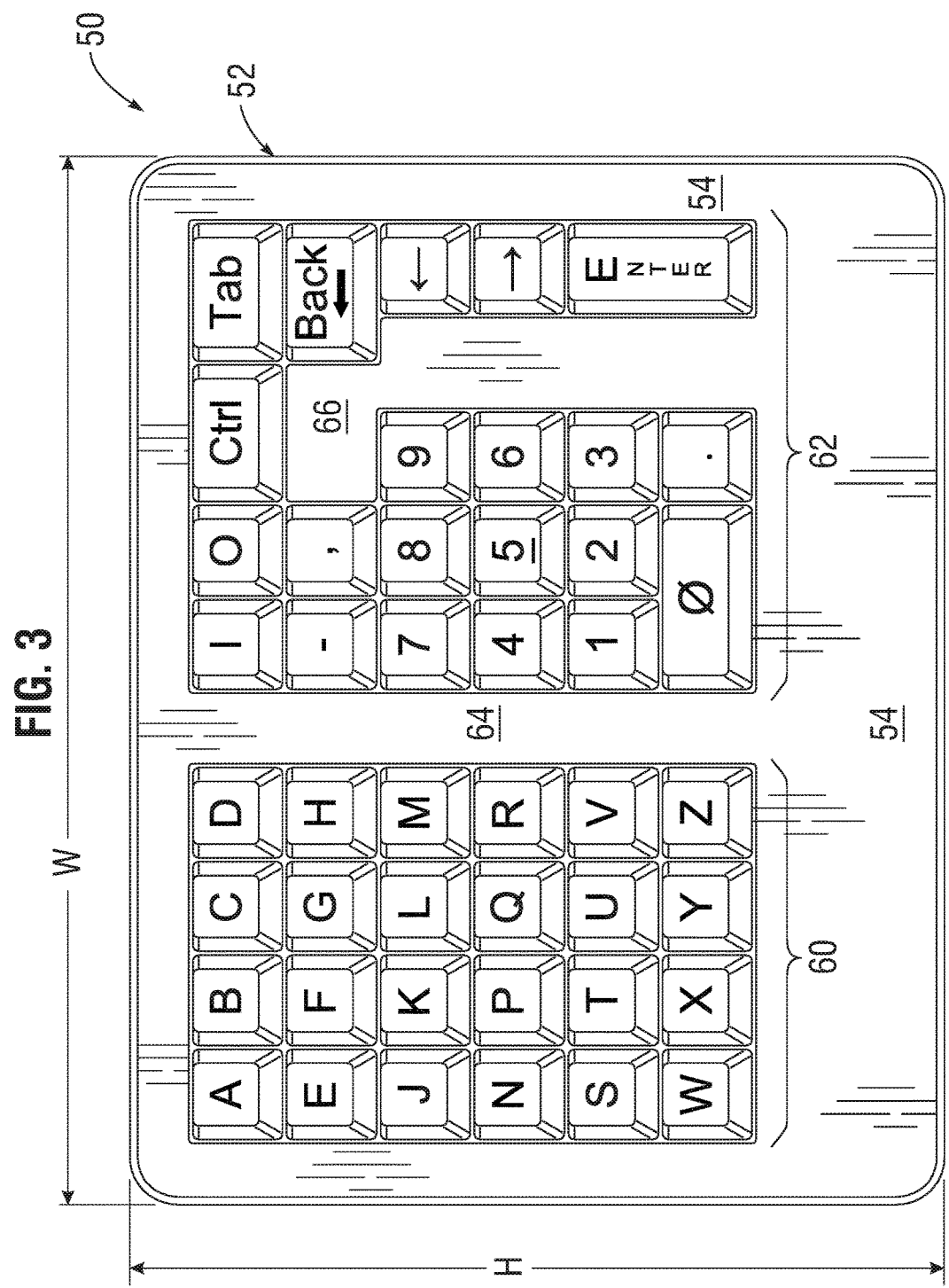
FIG. 3 is a top plan view of an alternative medical coding keyboard of the present application.

FIG. 3 is a top plan view of an alternative medical coding keyboard 50 of the present application. The keyboard 50 is similar in many respects to the keyboard 20 shown in FIGS. 1 and 2, with the exception that the key groups are slightly modified.

As before, the keyboard 50 includes a generally rectangular housing 52 (preferably molded plastic) including a peripheral frame or border region 54 surrounding two groups of keys. A first key group 60 includes just alphabetic keys and is identical to the first key group 22 in the earlier-described keyboard 20. That is, there are 24 alphabetic keys arranged from A-Z inclusive of all of the alphabetic except for "I" and "O." Likewise, the letter keys are arranged in four columns of six rows from top to bottom, and the first key group 60 is positioned on the left side of the rectangular housing 52. Of course, the first key group 60 may be positioned on the right side to accommodate alternate-handed users or preference.

A second key group 62 including alphabetic, numerical, punctuation and functional keys is positioned to the right of the first key group 60 with a relatively wide vertical key gap 64 therebetween. The second key group 62 is semi-segregated into function keys on the right separated by a key gap 66 from the rest of the keys in the group. The key gap 66 does not completely segregate the function keys from the rest of the keys, and an oversized control key at the top acts as a bridge between the two sets of keys. More specifically, the function keys on the right include the control key, and then the tab key, a backspace key, a left arrow key, a right arrow key, and an enter key arranged vertically on the right side of the second key group 62. Of the rest of the keys, a standard 11-key numerical keypad is present in the lower four rows, with a set of four keys above that. The four keys include the "I" and "O" keys directly above a hyphen or dash key and a comma key. The reader will note that the escape and space keys are eliminated in the alternative keyboard 50. Although these keys are useful in certain contexts, are not absolutely necessary for medical coding according to the ICD-10-PCS coding standard.

Consequently, the twenty-four alphabetic keys in the first key group 60, plus the twenty-one in the second key group 62 totals forty-five (45) keys, which is considered a practical minimum for medical coding. The additional "escape" and "space" keys included on the first keyboard 20 are helpful though not essential.

The alternative keyboard 50 only has the necessary keys for "Healthcare coding," and was built as a simple input device for coding to shorten the time it takes to find only the necessary keys used for all of these coding areas. Using the full-size keyboard is cumbersome and slows down the coding process and adds serious risk for error coding, and the smaller keyboard 50 improves both of those areas.

For coding:

ICD-10 CM/PCS—International Classification of Disease—$10^{th}$ revision Clinical Modification/Procedural Coding Systems (Hospital)

CPT-Current Procedural Terminology (Outpatient)

HCPCS Level II-Medical Durable Equipment and any other supplies etc.

DSM-IV The Diagnostic and Statistical Manual of Mental Disorders (Psychiatric Hospitalizations)

CDT—Current Dental Terminology

The Values of the disclosed Healthcare Coder Keyboards

These keys do not randomly repeat when pressed. The keys are so finger user-friendly they feel superior to regular keyboarding. This is "Cadillac Quality" compared to regular keyboards. The raised feature of each key provides excellent user contact. Less errors are thus made during coding. When pressed, the keys on the keyboard "register" every time without fail. There is no inconsistent behavior or "travel" by these keys, and there is excellent finger contact when pressed. There are no duplicate letters or numbers when pressed. There is no unusual key functioning, or sticking to be reported. There is no sound other than the engagement of the keys. Excellent key board quality. Certainly, an improvement to standard keyboards. This increases speed and ultimately production.

The keyboards disclosed herein may be used in conjunction with a regular keyboard. You can use either or at the same time. Simply swap to the regular keyboard to create sentences or physician queries. (Paragraph or sentences to be created to forward to physician for missing information or clinical errors with their documentation).

Additional features include:

Improved Accuracy—number of accepted claims on first pass (letters I, O have been relocated so they will not misrepresent number 1 and 0 ZERO.

ICD-10 PCS does not use letters I or O.

Productivity—number of cases coded due to smaller work area (keyboard)

Keyboard is smaller in size allowing additional desk area.

Portability

Right hand or Left hand use. One hand coding rather than searching all over standard keyboard for needed keys.

Facilitates only 45 necessary coding keys (always in capitol font) compared to standard long keyboard with 104 keys.

Works via USB port on any PC or laptop.

The keyboard can be used in conjunction (same time) as regular keyboard when necessary to create "coding query" to physician.

Focus is directly on coding, ICD-10 CM/PCS, CPT, HCPCS, DSM-5 and Dental coding.

Works with 3M Encoder

Computer Assisted Coding (CAC) Works with any system a regular keyboard does.

USB port activated

Ease of use that is typical of small keyboard tools

Functionality that exceeds that of large keyboard tools

Currently, there are very few regular keyboard typing classes offered anywhere. Coders are two-handed finger pressing using full size keyboard. This keyboard has improved functionality as it is strictly designed for healthcare coding. Easy to use one-handed.

Closing Comments

Throughout this description, the embodiments and examples shown should be considered as exemplars, rather than limitations on the apparatus and procedures disclosed or claimed. Although many of the examples presented herein involve specific combinations of elements, it should be understood that those elements may be combined in other ways to accomplish the same objectives. Elements and features discussed only in connection with one embodiment are not intended to be excluded from a similar role in other embodiments.

It is claimed:

1. A keyboard useful for medical coding, comprising:
   a housing enclosing keyboard circuitry and framing a plurality of keys connected to the circuitry and segregated into key groups, including:
   a first key group having just alphabetic keys inclusive of all the letters of the alphabet except for the letters I and O, and
   a second key group spaced from the first key group on the housing across a key gap and including a numeric keypad with the digits 0-9 and alphabetic keys with the letters I and O, wherein
   all alphabetic keys display uppercase letters and the circuitry is configured to send uppercase letter signals, and there is no shift key to switch to lowercase letters on the keyboard.

2. The keyboard of claim 1, wherein there are a total of no more than forty-seven total keys.

3. The keyboard of claim 2, wherein there are a total of forty-five keys.

4. The keyboard of claim 1, further including a third key group spaced from both the first and second key groups and having only function keys.

5. The keyboard of claim 1, wherein the second key group also includes function keys.

6. The keyboard of claim 1, wherein the alphabetic keys in the first key group are arranged in rows and columns in alphabetical order from the top left continuing along each row to the bottom right.

7. The keyboard of claim 1, wherein the keyboard housing has a width W of between about 25-30 cm, and a height H of between about 15-20 cm.

8. A keyboard useful for medical coding, comprising:
   a keyboard defining a keyboard face having a width W of between about 25-30 cm, and a height H of between about 15-20 cm;
   the keyboard face having thereon separate character keys segregated into a plurality of key groups spatially separated from each other across key gaps, wherein a first one of the key groups includes alphabetic keys inclusive of all the letters of the alphabet except for the letters I and O, and a second key group includes the alphabetic keys for the letters I and O, wherein
   all alphabetic keys display uppercase letters and keyboard circuitry provided for the keyboard is configured to send uppercase letter signals, and there is no shift key to switch to lowercase letters on the keyboard.

9. The keyboard of claim 8, wherein there are a total of no more than forty-seven total keys.

10. The keyboard of claim 8, wherein the second key group includes a numeric keypad, and there is a third key group spaced from both the first and second key groups and having only function keys.

11. The keyboard of claim 10, wherein the second key group also includes function keys.

12. The keyboard of claim 8, wherein the keyboard is a standalone item with a plastic keyboard housing defining the keyboard face.

13. The keyboard of claim 8, wherein the alphabetic keys in the first key group are arranged in rows and columns in alphabetical order from the top left continuing along each row to the bottom right.

14. A keyboard useful for medical coding, comprising:
   a first key group having alphabetic character keys arrayed in alphabetical order in a plurality of rows and columns inclusive of all the letters of the alphabet except for the letters I and O;
   keys for the letters I and O spaced from the first key group across a key gap, and
   wherein there are a maximum of forty-seven (47) total keys and all of the alphabetical keys are shown and configured to trigger key signals in uppercase with no shift key to permit them to convert to lowercase.

15. The keyboard of claim 14, wherein there are a maximum of forty-five (45) total keys.

16. The keyboard of claim 14, wherein there is a second key group including a numeric keypad and the letters I and O, and a third key group spaced from both the first and second key groups and having only function keys.

17. The keyboard of claim 14, wherein there is a second key group including the letters I and O and function keys.

18. The keyboard of claim 14, wherein the keyboard defines a keyboard face having a width W of between about 25-30 cm, and a height H of between about 15-20 cm.

19. The keyboard of claim 18, wherein the keyboard is a standalone item with a plastic keyboard housing defining the keyboard face.

20. The keyboard of claim 14, wherein the keyboard is a virtual keyboard superimposed on a display screen.

\* \* \* \* \*